United States Patent [19]

Raines

[11] Patent Number: 5,910,435
[45] Date of Patent: *Jun. 8, 1999

[54] METHOD OF FOLDING PROTEINS WITH SYNTHETIC DITHIOL CATALYSTS

[75] Inventor: Ronald T. Raines, Madison, Wis.

[73] Assignee: Wisconsin Alumni Research Foundation, Madison, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/687,276

[22] Filed: Jul. 25, 1996

[51] Int. Cl.$^6$ .............................. C12N 9/96; C12N 9/00; C12P 21/06; A61K 38/00; C07K 1/00
[52] U.S. Cl. ..................... 435/188; 435/69.1; 435/183; 530/345; 530/402
[58] Field of Search .................................. 530/345, 402; 435/183, 69.1, 188

[56] References Cited

U.S. PATENT DOCUMENTS 5,235,043  8/1993  Collins et al. ........................... 530/399
5,460,806  10/1995  Whitesides et al. ................... 424/70.5

OTHER PUBLICATIONS

Creighton (1985) J. Phys. Chem., 89(12), "The Problem of How and Why Proteins Adopt Folded Conformations", pp. 2452–2459.

Tam (1991) J. Am. Chem. Soc., 113(17), "Disulfide Bond Formation in Peptides by Dimethyl Sulfoxide. Scope and Applications", pp. 6657–6662.

Roberts et al. (1986) Biochemistry, 25(19), "Reactivity of Small Thiolate Anions and Cysteine–25 in Papain toward Methyl Methanesulfonate", pp. 5595–5601.

Lees et al. (1993) J. Org. Chem., 58(3), "Equilibrium Constants for Thiol–Disulfide Interchange Reactions: A Coherent, Corrected Set", pp. 642–647.

Singh et al. (1994) Bioorg. Chem., 22(1), "Reagents for Rapid Reduction of Native Disulfide Bonds in Proteins", pp. 109–115.

Ruoppolo et al. (1995) Biochemistry, 34(29), "Refolding by Disulfide Isomerization: The Mixed Disulfide between Ribonuclease $T_1$ and Glutathione as a Model Refolding Substrate", pp. 9380–9388.

Chivers et al., "The CXXC motif: imperatives for the formation of native disulfide bonds in the cell," *The EMBO Journal* 15:101–109 (1996).

Edman et al., "Sequence of protein disulphide isomerase and implications of its relationship to thioredoxin," *Nature* 317:267–270 (1985).

(List continued on next page.)

Primary Examiner—Jon P. Weber
Attorney, Agent, or Firm—Quarles & Brady

[57] ABSTRACT

An analysis of the protein folding characteristics of the eukaryotic protein folding enzyme protein disulfide isomerase (PDI) led to a study of the minimally sufficient motif for catalytic activity of that enzyme as well as the prokaryotic enzyme thioredoxin. Based on such study, a model for this catalytic activity was developed which was used to predict what non-protein catalysts might substitute for this enzymatic activity. Based on this analysis, it was predicted that a small molecular weight dithiol molecule having a $pK_a$ of less than about 8.0 and an $E^{o\prime}$ of more than about −0.25 V could catalyze the formation of proper disulfide bonds in a eukaryotic protein. Subsequently, it was verified that such a dithiol, such as the exemplary molecule N,N'-bis(2-mercaptoacetyl)-1,2-diaminocyclohexane (BMC), is capable of catalyzing the proper formation of disulfide bonds, and the proper folding of proteins, both in vivo and in vitro. This permits a small organic molecule to be substituted for an enzymatic system in protein synthesis.

9 Claims, 5 Drawing Sheets

OTHER PUBLICATIONS

Kasina et al., "Issue Distribution Properties of Technetium–99m–Diamide–Dimercaptide Complexes and Potential Use as Renal Radiopharmaceuticals," *J. Med. Chem.* 29:1933–1940 (1986).

Laboissiere et al., "Production of Rat Protein Disulfide Isomerase in *Saccharomyces cerevisiae*," *Protein Expression and Purification* 6:700–706 (1995).

Laboissiere et al., "The Essential Function of Protein–disulfide Isomerase is To Unscramble Non–native Disulfide Bonds," *The Journal of Biological Chemistry* 270: 28006–28009 (1995).

Lamoureux et al., "Synthesis of Dithiols as Reducing Agents for Disulfides in Neutral Aqueous Solution and Comparison of Reduction Potentials," *J. Org. Chem.* 58:633–641 (1993).

Singh et al., "A Reagent for Reduction of Disulfide Bonds in Proteins That Reduces Disulfide Bonds Faster Than Does Dithiothreitol," *J. Org. Chem.* 56:2332–2337 (1991).

Singh et al., "Reagents for Rapid Reduction of Disulfide Bonds," *Methods in Enzymology* 251: 167–173 (1995).

Thomas et al, "Altered protein folding may be the moleculare basis of most cases of cystic fibrosis," *FEBS* 312:7–9 (1992).

Thomas et al., "Defective protein folding as a basis of human disease," *TIBS* 20:456–459 (1995).

BMC

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (v) FRAGMENT TYPE: internal (xi) SEQUENCE DESCRIPTION: SEQ ID NO:1:

Cys Xaa Xaa Cys
   1

(2) INFORMATION FOR SEQ ID NO:2:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (v) FRAGMENT TYPE: internal (xi) SEQUENCE DESCRIPTION: SEQ ID NO:2:

Cys Gly His Cys
   1

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:3:

Cys Gly Pro Cys

METHOD OF FOLDING PROTEINS WITH SYNTHETIC DITHIOL CATALYSTS

This invention was made with U.S. government support awarded by NIH Grant No. GM44783 and NSF Grant No. MCB 9057203. The United States has certain rights in this invention.

FIELD OF THE INVENTION

The present invention relates to the general field of molecular biology and relates, in particular, to a technique using an organic molecule to catalyze the proper folding of proteins produced outside of their native hosts.

BACKGROUND OF THE INVENTION

Proteins are linear polymers composed of subunit monomers known as amino acids. The chemical content of a protein is specified by the order of amino acids that make up the polymer, referred to as its primary structure. The function of a protein is dependent, in addition to the primary structure, on what is referred to as tertiary structure. Tertiary structure refers to the three-dimensional shape into which the protein is bent and fixed as part of the protein expression mechanism in the cells of its host organisms. A critical component in determining the tertiary structure of a protein is the formation of disulfide bonds between any cysteine residues present in the protein. The disulfide bonds between cysteine residues constrain the protein to certain three-dimensional shapes, or tertiary structures. The formation of proper tertiary structure for biological activity takes place naturally in eukaryotic cells during the protein expression and processing system which takes place in the endoplasmic reticulum of eukaryotic cells.

It has become a common procedure of modern biotechnology to produce proteins in heterologous hosts, that is in organisms which do not normally produce the desired protein. In fact, it is most economical, and therefore most desirable, when producing human and mammalian proteins of potential therapeutic or industrial utility, to produce those proteins in prokaryotic organisms, such as the common bacteria E. coli. The main reasons for desiring a prokaryotic host relate simply to cost and the related convenience and experience base built up by the modern biotechnology industry in the fermentation, cultivation and purification of prokaryotic organisms.

One of the major problems in the use of a prokaryotic host to express a mammalian protein, or any protein from a eukaryotic organism, is the problem of proper tertiary structure of the expressed protein. Because the protein expression and assembly process is much different in heterologous hosts, such prokaryotic hosts do not always form correct disulfide bonds during the process of protein formation. The result is that heterologous mammalian proteins produced in prokaryotic hosts are often recovered from the hosts in a variety of different tertiary structures, only some portion of which will have the desired biological activity. This results in an inefficiency in the protein production system, as well as adding a purification problem since the proteins having the proper tertiary structure and biological activity often must be separated from those which are improperly folded.

The process of eukaryotic protein folding, which occurs in the endoplasmic reticulum of eukaryotic cells, is only partially understood. It is known that eukaryotic cells possess an enzyme called protein disulfide isomerase, abbreviated PDI. PDI is a large 57 kilodalton enzyme which helps to ensure that disulfide bonds necessary for biological activity of proteins are formed correctly. One or more forms of PDI are found in the endoplasmic reticulae of all eukaryotic organisms.

Because the proper folding of proteins is of significant scientific and commercial interest, systems have been designed to help to study protein folding. One such system is based on a yeast cells which lack a nuclear gene for the PDI enzyme, and are therefore incapable of catalyzing the formation of the proper disulfide bonds required for biological activity of proteins. Such yeast cells can be grown so long as they harbor a plasmid that produces PDI, but the cells promptly expire when the plasmid PDI is removed. The ability of mutant, altered, or engineered forms of PDI to rescue the PDI-deficient yeast cultures from death is a test of the suitability of such altered isoforms to properly fold proteins. Investigation into the function of PDI, and its use in the unscrambling of non-native disulfide bonds, is described by Laboissiere et al., J. Biol. Chem. 270:47:28006–28009 (1995). Based on this test system, it has been possible to determine that the motif for PDI activity consists of a particular amino acid domain. This domain is shared in common with the reducing bacterial enzyme thioredoxin. The domain has the consensus sequence Cys-X-X-Cys (SEQ ID NO: 1 or C-X-X-C, where X is an amino acid, Edman, Nature 317:267–270 (1985).

Separately, for a variety of other reasons it is often desirable to break disulfide bonds in proteins by reducing them. Accordingly, some investigation has been conducted on organic molecules which may be used for the rapid reduction of disulfide bonds in proteins. A group led by Whitesides, at Harvard, has published a series of papers on various synthetic reagents which may be used for reducing disulfide bonds. Singh and Whitesides, J. Org. Chem. 56:2332–2337 (1991); Lamoureux and Whitesides, J. Org. Chem. 58:633–641 (1993); and Singh et al., Methods in Enzymology 251:167–173 (1995). The Whitesides group sought to find an idealized organic molecule which would have a low $pK_a$ value and a high value for its reduction potential. Using these criteria, this group identified a particular organic molecule, 2,5-dimercaptotetramethyl adipamide as the ideal molecule for use in reducing disulfide bonds, as illustrated in U.S. Pat. No. 5,378,813. Several other synthetic dithiols are also described by Whitesides group with low $pK_a$ and high reduction potential.

SUMMARY OF THE INVENTION

The present invention is summarized in that it has been found that organic dithiol molecules having a $pK_a$ of less than about 8.0 and a standard reduction potential (E°') of greater than about −0.25 volts are capable of catalyzing the formation of proper disulfide bonds in proteins, in the complete absence of PDI, both in vivo and in vitro.

The present invention is further summarized in that a method for defining dithiol molecules which are capable of catalyzing the proper formation of tertiary structure in proteins is defined, such that additional molecules capable of catalyzing such reaction can be created and identified.

It is a feature of the present invention in that it has been found that the dithiol compound BMC is capable both in vivo and in vitro of catalyzing the formation of the proper biologically active form of eukaryotic proteins produced in non-eukaryotic systems.

It is an advantage of the present invention in that the addition of a simple organic dithiol molecule permits the expression of eukaryotic proteins in hosts in such a fashion that the proteins are expressed in their biologically active tertiary structure.

It is an advantage of the present invention in that it may be used both in vivo and in vitro to produce and correct tertiary structure of proteins in an efficient and economical manner.

Other objects, advantages and features of the present invention will become apparent from the following specification when taken in conjunction with the accompanying drawings.

BRIEF DESCRIPTION OF THE DRAWING FIGURES

DETAILED DESCRIPTION OF THE INVENTION

Figure 1:
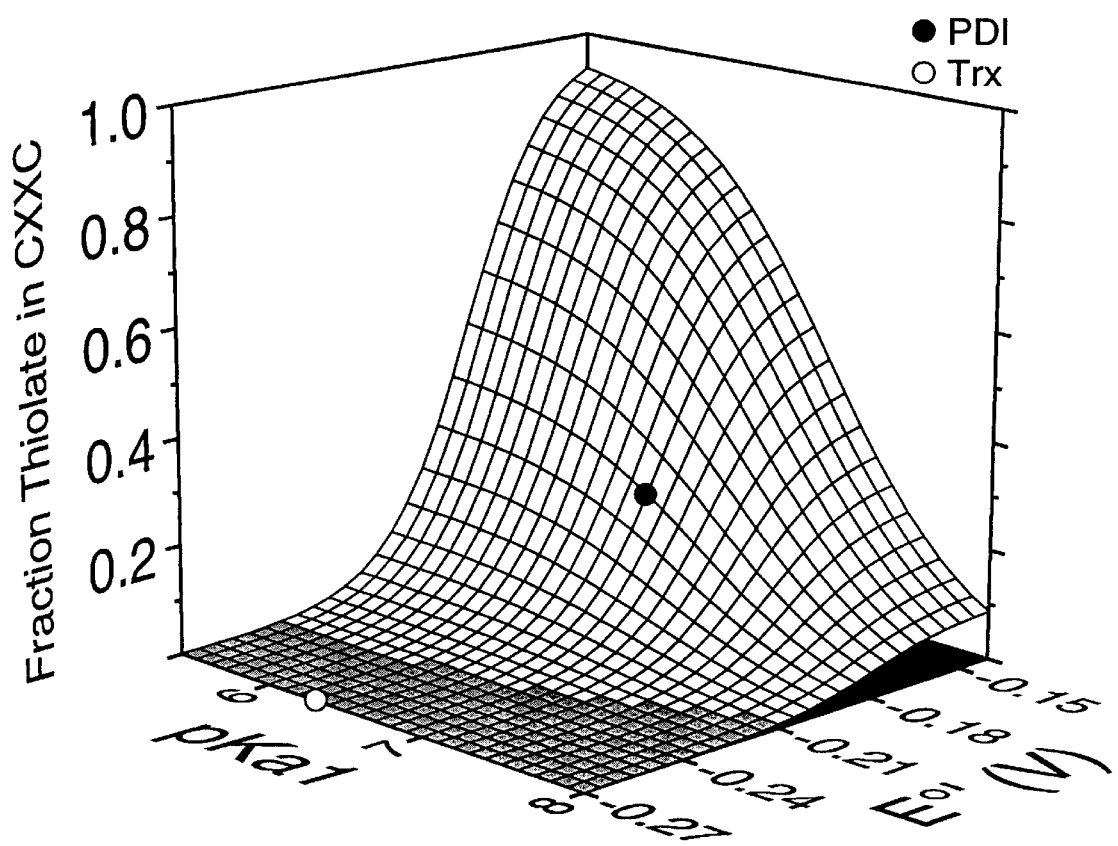
FIG. 1 is a graphical illustration of the characteristics of molecules for use within the present invention.

The present invention is summarized in that it has been found that a defined class of small organic dithiol molecules is capable, both in vitro and in vivo, of catalyzing the proper formation of disulfide bonds in eukaryotic proteins, to ensure that proper tertiary structure, and therefore proper biological activity, is achieved. In other words, it has been found that a class of simple small organic molecules is capable of substituting for the previously poorly understood enzymatic systems present in eukaryotic cells to ensure the proper formation of the tertiary structure of complex proteins. These non-protein molecules function as synthetic protein folding catalysts. This discovery dramatically simplifies the problem of the production of biologically active eukaryotic proteins in prokaryotic systems and, in fact, in cell free in vitro systems as well.

The investigation which led to the present invention began with a study of the functional domain of the PDI protein. A study was conducted in the laboratory of the inventor here to further and better understand the catalytic motif of the PDI molecule. That study was conducted using mutant PDI deficient yeast. Various forms of mutant PDI were added to the medium in which the yeast were cultured, to discover which variants on the PDI enzymatic motif were capable of rescuing the yeast, thereby indicating which variations on the motif are capable of the catalysis of proper protein folding in the yeast system. The enzymatic motif of PDI is the four amino acid domain Cys-Gly-His-Cys (SEQ ID NO: 2). It was discovered that the first cysteine residue in the active site is absolutely critical to PDI activity. This particular cysteine in the PDI molecule has a low $pK_a$ (6.7). $pK_a$ refers to the negative log of the acid dissociation constant of the molecule. A lower $pK_a$ means that the molecule is more easily ionized. A $pK_a$ of 6.7 means that at the pH present in physiological systems, over 50% of the cysteine residues in the PDI molecules present in the system would be ionized. The ionized thiolate is a good nucleophile which indicates a strong implication for the initial step in the formation of disulfide bonds.

Theorizing that other enzymes might be capable of similarly catalyzing the proper formation of disulfide bonds, our group then went on to conduct similar work with the enzyme thioredoxin from *E. coli*. Thioredoxin is a prokaryotic functional homolog of PDI, possessing two similar domains out of the four present in PDI. Thioredoxin is a much smaller protein, 12 kilodalton, found in the cytoplasm of *E. coli*, and not heretofore understood to be involved in protein re-folding. Attempts to complement the PDI deficient yeast with thioredoxin failed.

To explore the differences between thioredoxin and PDI, a series of mutants of the thioredoxin active site (Cys-Gly-Pro-Cys), as shown in SEQ ID NO: 3, were made and to explore whether any of these mutants could rescue PDI-deficient yeast. Several of the mutants successfully complemented and rescued the PDI deficient yeast cultures. With information in hand about which mutants did or did not rescue the yeast, it became possible to analyze the steric and energy constraints of the successful mutants to determine what parameters were important in a catalyst successfully rescuing the PDI deficient yeast. Such analysis is reported in Chivers et al. *EMBO I.*, 15:2659–2667. (1996).

This understanding suggested what an optimal catalyst to substitute for PDI should have. The catalyst should have two thiol groups, a relatively high standard reduction potential $E°'$ and a relatively high acid dissociation constant or a low $pK_a$. This can be best understood with reference to FIG. 3.

Figure 3:
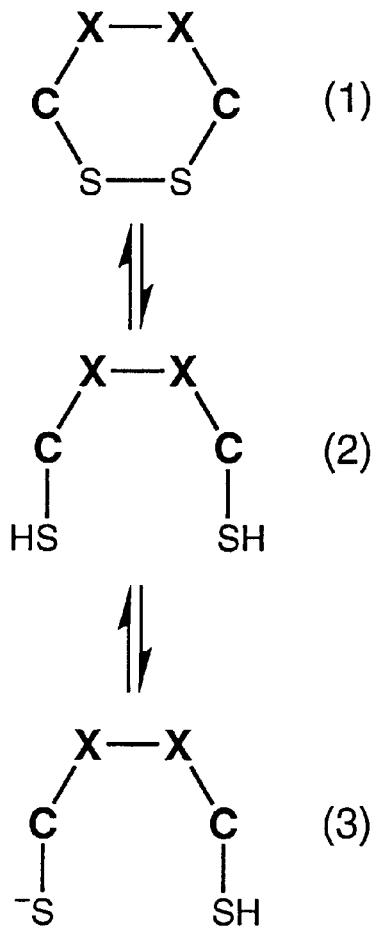
FIG. 3 is a schematic illustration of the three potential states of a classic dithiol motif capable of catalyzing the disulfide bond reactions between cysteine residues in a protein.

In molecule species 1 in FIG. 3, a protein motif is shown of the generic formula C-X-X-C (SEQ. ID NO: 1). The molecule 1 is shown oxidized with a disulfide bond between the sulfurs of the cysteine residues. In aqueous solution at physiological conditions, the species 1 exists in equilibrium with species 2, which is the same motif with the disulfide bond reduced. The relative proportion of species 1 and species 2 present at physiological conditions is determined by the standard reduction potential, $E°'$, of the molecule. Species 2 is then in equilibrium with species 3, which is the same molecule, which has now donated a proton to the solution. The relative proportions between species 2 and species 3 are determined by the acid dissociation constant of the molecule. Molecules having a $pK_a$ of less than about 8.0 will exist under physiological conditions in species 3 in relative abundance. The preferred thiolate molecule for use within the present invention should exist at physiological conditions in significant proportion in species 3.

Figure 2:
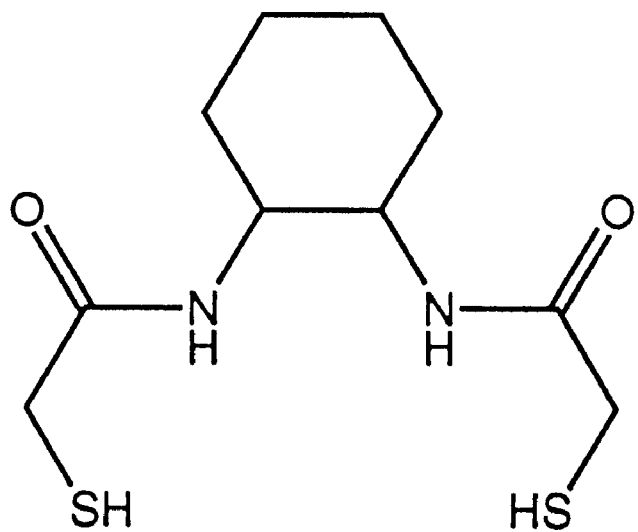
FIG. 2 is a chemical diagram of the BMC molecule, a species of dithiol useful within the present invention.

Now, having understood what conditions were necessary and sufficient to operate as a thiolate group based protein folding enzyme, it was then possible to imagine that a simple organic molecule, rather than a protein, could substitute for PDI and its enzymatic function. The literature revealed that Whitesides et al. had investigated various dithiol molecules as potential reducing agents for disulfide bonds. However, Whitesides' group, which was interested only in reducing disulfide linkages, was not as interested in molecules which had high reduction potentials, since that would be contrary to the objective of their research. Based on the chemistry published by Whitesides' group, an organic non-protein thiolate candidate molecule was selected. This molecule, N,N'-bis(2-mercaptoacetyl)-1,2-diaminocyclohexane, referred to as BMC, has its chemical structure illustrated in FIG. 2. This compound was initially synthesized by Kasina et al. *J. Med. Chem.* 29:1933–1940 (1986). The chemical synthesis of this molecule can also be performed by the methods described by Lamoureux and Whitesides, *J. Org. Chem.* 58:633–641 (1993). It was found that the BMC molecule was capable, and completely adequate by itself, to rescue PDI-deficient mutant yeast cultures. In other words, this single small organic molecule performed in vivo a function sufficient to substitute for a naturally-occurring enzyme, i.e. PDI. This demonstrates that it is possible to design small organic dithiol molecules, such as BMC, which are capable and sufficient in and of themselves to catalyze proper disulfide formation and proper tertiary structure of eukaryotic proteins produced outside of eukaryotic cells.

It is specifically envisioned that there is a class of dithiol catalysts which will suffice to form proper disulfide bonds and proper tertiary structure in eukaryotic proteins. To catalyze efficiently the isomerization of disulfide bonds, the dithiol molecule must have two attributes. First, one or both of its thiol groups must be easily ionized under physiological conditions. To accomplish this, the molecule must have a $pK_a$ that is less than about 8.0, and preferably close to or lower than 7.0. The reason for this requirement is only that an ionized thiol group, or thiolate, is nucleophilic in aqueous solution. Because the catalysis reaction requires that the catalyst perform a nucleophilic attack on the disulfide bond, only dithiols with low $pK_a$s can act as the catalyst.

Second, the dithiol must be able to form an intramolecular disulfide bond, but not form this bond too easily. If the intramolecular disulfide bond forms too easily under physiological conditions, that is to say has an $E^{o\prime}$ much less than −0.18 volts, then the necessary nucleophilic thiol would not exist in any event. The formation of a disulfide bond is important, however, to rescue the catalyst from an intramolecular disulfide bond that is too stable to react further. In general, a dithiol should have an $E^{o\prime}$ of more than about −0.25 V.

Thus, in its simplest definition, a synthetic protein catalyst in accordance with the present invention is an organic dithiol with a $pK_a$ of less than about 8.0 and an $E^{o\prime}$ of more than about −0.25 V. Based on this simple understanding, the inventor here selected a dithiol molecule, BMC, and, as demonstrated by the data below, has shown that that molecule is adequate alone to catalyze the formation of proper disulfide bonds in a eukaryotic protein.

Although sample criteria for selection of dithiol protein folding catalysts, based on simple evaluation of $pK_a$ and $E^{o\prime}$, as described above, is adequate, the actual relationship between these parameters is a bit more complex. In fact, based on studies of the thioredoxin catalytic motifs, a generalized formula has been derived to determine which dithiols will serve this function.

The equation derived to describe dithiol catalysts is:

$$\text{fraction thiolate} = \left[\frac{1}{1+e^{-\frac{nF}{RT}(0.18\text{ V}+E^{o\prime})}}\right]\left[1-\left(\frac{1}{1+10^{7.0-pK_{a1}}}\right)\left(\frac{1}{1+10^{7.0-pK_{a2}}}\right)\right] \quad (1)$$

where n=2, F=96,487 C/mol, R=8.314 J/(K.mol), and T~310 K. The values $pK_{a1}$ and $pK_{a2}$ refer to the $pK_a$s of the first and second thiol groups.

In the above equation number 1, the right hand side of the equation includes two terms. The first term derives from the Nernst equation, and it describes the fraction of the dithiol catalyst that is in the reduced form in an environment in which the $E^{o\prime}$=~−0.18 volts. This condition describes the endoplasmic reticulum, where disulfide bonds are formed in eukaryotic cells. The second term derives from the Henderson-Hasslebach equation, and it describes the fraction of the reduced thiol form that has at least one thiol group ionized in an environment at a pH equal approximately 7.0, again such as exists in the endoplasmic reticulum. The surface defined by this equation is illustrated in FIG. 1.

To utilize equation 1 in selection of a dithiol catalyst, consider a dithiol catalyst which has an $E^{o\prime}$=−0.18 volts, a $pK_{a1}$=7.0 and a $pK_{a2}$=9.0. In the endoplasmic reticulum, this hypothetical catalyst would be half reduced and half oxidized because its $E^{o\prime}$ is the same as that of the environment. Accordingly the first term in equation 1 would be equal to one-half. This reduced form can only exist in four states, one state with neither thiol group ionized, one state with both thiol groups ionized, and two states in which one thiol group is ionized and the other is not. The fraction of the reduced molecules that contain a thiolate, i.e. an ionized thiol group, is most easily calculated from the fraction that is fully protonated. Because the $pK_a$ of thiol group 1 is the same as the pH of the endoplasmic reticulum, the thiol of group 1 would be protonated in half of the reduced molecules. The second thiol group, in contrast to thiol group 1, has a $pK_a$ that is two units higher than the pH of the endoplasmic reticulum. Thus the second thiol group would be protonated in about 99% of the molecules. So both thiol groups would be protonated in about half of the reduced molecules and about half of the molecules would have one or both of the thiols in the thiolate form. Accordingly the second term would equal about one-half (actually 51 divided by 101) and the thiolate fraction of this hypothetical catalyst would therefore be about one-quarter.

The mutant E. coli thioredoxins described above were used to determine the combinations of $E^{o\prime}$ and $pK_a$ that can give rise to the catalysis of disulfide bond isomerization in a eukaryotic cell. This data revealed that several combinations of $E^{o\prime}$ and $pK_a$ did indeed provide functional protein catalysis. In addition it was found that the fraction thiolate, as calculated by equation 1 above, correlated with the viability of cells contained in the dithiol catalyst. This result highlights the importance of the "fraction thiolate" as a parameter to describe successful catalysts. The same parameter is applicable both to protein and non-protein catalysts. The lowest fraction thiolate that gave rise to a healthy viable population of PDI mutant yeast was fraction thiolate equal 0.011 as in the mutant of thioredoxin having the enzymatic group CGHC. This requirement seems to be a minimum one. In other words, for a successful disulfide catalyst, the fraction thiolate must be greater than 0.01 as defined in the equation:

$$\left[\frac{1}{1+e^{-\frac{nF}{RT}(0.18\text{ V}+E^{o\prime})}}\right]\left[1-\left(\frac{1}{1+10^{7.0-pK_{a1}}}\right)\left(\frac{1}{1+10^{7.0-pK_{a2}}}\right)\right] > 0.01 \quad (2)$$

Another way to relate the three variables, i.e. the fraction thiolate, $E^{o\prime}$, and $pK_a$ is on a three-dimensional plot. Such a plot is shown in FIG. 1. The values of fraction thiolate for wild-type PDI and wild-type thioredoxin (Trx) are indicated on the plot in FIG. 1. In this plot, it is assumed that $pK_{a2}$ is much greater than 7.0, as is true for both PDI and thioredoxin. This condition, or at least a condition in which the $pK_a$ for the second thiol group is much greater than the $pK_a$ for the first thiol group, is also likely to be true in desirable synthetic dithiols, because the negative charge formed upon the deprotonation of one thiol group will make more difficult the deprotonation of the second thiol group. The boundary between the grey and white surfaces in the three-dimensional graph of FIG. 1 is a line drawn for a fraction thiolate equals 0.01. Any dithiol catalyst on the white surface obeys equation 2 above. It is intended here to specify that synthetic dithiols on this white surface will prove satisfactory for an organic protein folding catalyst.

In addition to the production of eukaryotic proteins in non-eukaryotic systems, the ability to specify small organic molecules which act to correct the folding of eukaryotic proteins suggests other possible utilities for these molecules. Several important diseases, particularly genetic diseases, have been implicated as arising from defects in protein folding. These diseases include cystic fibrosis, familial hyperchlosterolemia, alpha 1-antitrypsin deficiency, Marfan syndrome, amylotrophic lateral sclerosis, osteogenesis imperfecta, and certain forms of cancer. The synthetic catalysts described herein which serve as protein folding catalysts may be the basis for therapies for these and other protein folding related diseases. It is specifically contemplated that the administration of a synthetic folding catalyst agent could benefit a patient by one of three possible mechanisms. The first is that a synthetic protein folding catalyst could act directly by catalyzing the proper folding of the aberrant protein responsible for the etiology of the disease. A second mechanism is the synthetic folding catalyst could act indirectly by making the protein folding machinery of the diseased cells more efficient overall and thereby help that native mechanism to better fold a higher percentage of the improperly folded protein. Thirdly, a synthetic folding catalyst could ameliorate the symptom of a disease rather than its cause by catalyzing the folding of other proteins whose folding is in turn affected by the disease.

As an example, consider the disease cystic fibrosis. This disease is a fatal genetic disease that arises from mutations in the gene encoding the cystic fibrosis conductance regulator (CFTR) protein. Approximately 70% of the cases of cystic fibrosis result from the loss of a phenylalanine residue which is amino acid 508 in the CFTR protein sequence. The deletion of the phenylalanine residue results in improper processing of the ΔF508 CFTR. Properly processed ΔF508 CFTR is functional, so the mutation only affects the folding of the protein on the way to the final product. It is speculated that administration of synthetic protein folding catalyst such as that described in this patent application could potentially benefit a patient with cystic fibrosis. The administration could be by inhalant of an aerosol deposition of the synthetic protein folding catalyst. The synthetic protein folding catalyst could act to assist the folding of the ΔF508 CFTR, either directly or indirectly. Alternatively, the synthetic protein folding catalyst could ameliorate the symptoms of the disease including respiratory distress and progressive lung destruction. Synthetic protein folding catalysts of the type described in this patent application are likely to be well tolerated by patients because the $E^{o'}$ of synthetic protein folding enzymes, unlike for example, DTT, is similar to the $E^{o'}$ of eukaryotic cells.

EXAMPLE 1

Synthesis of BMC

Figure 4:
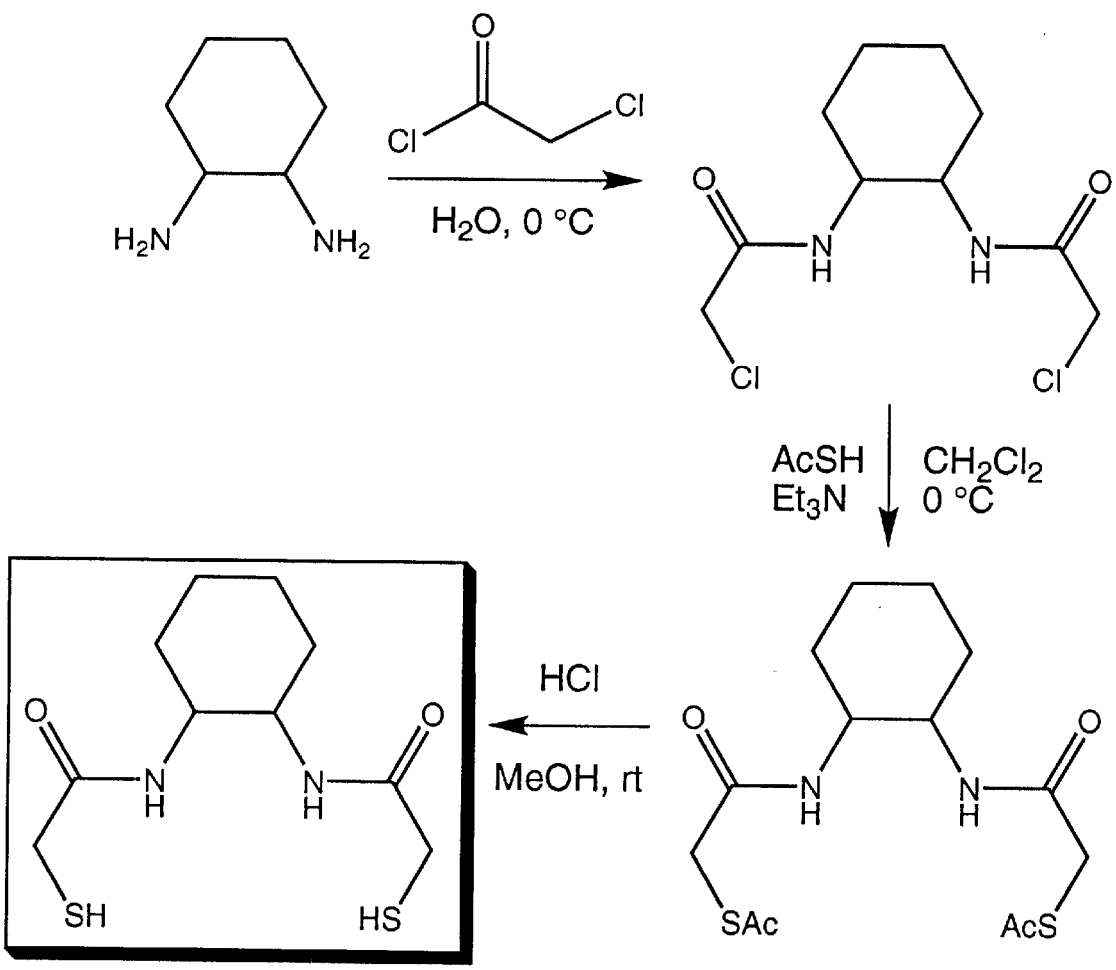
FIG. 4 is an illustration of the route of synthesis of bis (2-mercaptoacetyl) -1,2-diaminocyclohexame (BMC) as described in an example below.

BMC was synthesized by the route shown in FIG. 4, similar to the route reported by Kasina, *J. Med. Chem.* 29:1933–1940 (1986); Lamoureux et al., *J. Org. Chem.* 58:633–641 (1993).

1,2-Diaminocyclohexane was purchased from Aldrich (Milwaukee) as a mixture of the trans and cis isomers, and was used without further purification. Solvents and other reagents were purchased from commercial source and used without further purification. 1,2-Diaminocyclohexane (1.1 g, 10 mmol) and $K_2CO_3$ (2.8 g, 20 mmol) were dissolved in 50 mL of ice-cold distilled water. Chloroacetyl chloride (1.7 mL, 21 mmol) was added dropwise and with stirring in this solution. The resulting cloudy white mixture was stirred at 0° C. for 1 hour. The precipitate was collected from the cold mixture by filtration through a Buchner funnel. The precipitate was washed with cold distilled water, and dried under reduced pressure. The bis(chloroacetyl) product (0.68 g, 25%) was obtained as a white powder, which was judged to be pure by NMR spectroscopic analysis.

The bis(chloroacetyl) product (0.67 g, 2.5 mmol) was dissolved in 120 mL of methylene chloride, and this solution was cooled to 0° C. Thiolacetic acid (0.42 mL, 5.8 mmol) was added dropwise and with stirring to the cooled solution. Then, triethylamine (0.80 mL, 5.8 mmol) was added dropwise and with stirring. The resulting solution was allowed to warm slowly to room temperature, and stirred under nitrogen gas for 20 hours. The reaction was quenched by the addition of aqueous acetic acid buffer, pH 4. The layers were separated in a separatory funnel, and the organic layer was dried, filtered, and concentrated to yield a white powder. This powder was purified by recrystallization from ethyl acetate. The bis(thiolacetate) product (0.25 g, 30%) was obtained as a white powder, which was judged to be pure by NMR spectroscopic analysis.

The bis(thiolacetate) (0.24 g, 0.7 mmol) was dissolved in 15 mL of 1.2 M HCl in methanol. The resulting clear solution was incubated at room temperature for 20 hours. The solvent was removed under reduced pressure to yield a yellow oil. The oil was dissolved in a minimal amount of methanol and the resulting solution was cooled in a dry ice/acetone bath. The supernatant was decanted and the white precipitate was dried under reduced pressure to yield BMC (102 mg, 56%) as a white solid, which was judged to be pure by NMR spectroscopic analysis. BMC was judged to be a 6.5:1 mixture of the trans to cis isomers by integration of the NMR spectral peaks.

EXAMPLE 2

Rescue of PDI-deficient yeast.

The ability of a synthetic diol protein catalyst to catalyze protein folding in vivo was tested by its ability to replace the function of PDI in a eukaryotic cell. The cells used for this procedure were pdi1Δ *Saccharomyces cerevisiae*, which have a deletion in their PDI1 gene rendering the expressed enzyme dysfunctional. The PDI1 gene is an essential gene for survival of *S. cerevisiae*. To enable these cells to live, the cells contain a plasmid that directs expression of *S. cerevisiae* PDI. This plasmid also directs the expression of the UPA3 gene product. These cells were streaked onto plates of minimal medium containing 5-fluoroorotic acid (5-FOA) which makes the URA3 gene product toxic to *S. cerevisiae*. Accordingly, this selects against presence of the plasmid and surviving cells will have neither the plasmid nor PDI.

This test was run with plates containing 5-FOA which also contained 0 or 10 mM BMC. Surviving colonies appeared on the 10 mM BMC plate in 5 days. No colonies survived on the plate without BMC.

Cells from the colonies rescued with BMC were then plated onto rich medium without BMC. The rescued cells failed to survive on this medium even though all necessary yeast nutrients were present.

This same procedure was repeated with the disulfide bond reducing agent dithiothrietol (DTT). DTT is a low molecular weight dithiol with a higher $pK_a$ and a lower $E^{o'}$ than BMC. When DTT was used, no yeast colonies could be rescued from the PDI-deficient strains after addition of 5-FOA.

This demonstrates that BMC can replace PDI in a eukaryotic cell in vivo to unscramble non-native disulfide bonds.

Thus, BMC can act functionally like those mutant thioredoxins that can substitute for the activity of PDI in vivo.

EXAMPLE 3

Processing of in vitro produced proteins.

In Vitro Assay of BMC Activity

Disulfide bonds form readily in an oxidizing environment. These disulfide bonds may not, however, be the ones that exist in the native, active conformation of a protein. The desirable property in a synthetic protein foldase is the ability to catalyze the unscrambling of non-native disulfide bonds. The ability of BMC to catalyze the unscrambling of non-native disulfide bonds in vitro was assayed by a method similar to that reported previously by our group and others. Laboissiere et al, *Protein Express. Purif.* 6:700–706 (1995).

This assay is based on the disulfide bonds in ribonuclease A, a well-characterized enzyme. In its native, enzymatically active conformation, ribonuclease A has eight cysteine residues which participate in four specific disulfide bonds. The substrate for this assay is "scrambled" ribonuclease A, which is a mixture of ribonuclease A molecules having non-native disulfide bonds. (There are 105 ways to form four disulfide bonds from eight cysteine residues.) Because the native disulfide bonds are necessary for high enzymatic activity, scrambled ribonuclease has much lower enzymatic activity that does native ribonuclease A. Scrambled ribonuclease A was purchased from Sigma Chemical (St. Louis, Mo.).

In the assay, BMC was tested for its ability to catalyze the regain of enzymatic activity in scrambled ribonuclease A. This regain in activity can only occur by the isomerization (or unscrambling) of the non-native disulfide bonds. The reactions were initiated by the addition of 1.0 $\mu$L of a 0.50 mg/mL solution of scrambled RNase A in 100 mM aqueous acetic acid to 99 $\mu$L of 25 mM Tris-HCl buffer, pH 7.6, containing MBC (0, 20, or 200 $\mu$M), reduced glutathione (1 mM), and oxidized glutathione (0.2 mM). The glutathione in the reaction mixture provides a buffer that keeps the reduction potential constant and at a value that allows for disulfide bond formation. These conditions mimic the conditions in the endoplasmic reticulum of eukaryotic cells. The reaction mixture was incubated at 30° C. At known time intervals (typically 30 minutes), a 10 $\mu$L aliquot was removed and tested for the regain of ribonucleolytic activity. In this test, the aliquot was added to 500 $\mu$L of 100 mM MES-HCl buffer, pH 6.0, containing 100 mM NaCl and 10 mM poly(C) RNA, which is a substrate for ribonuclease A. Ribonucleolytic activity was monitored by following the change in absorbance at 238 nm which accompanies the cleavage of poly(C) by enzymatically active ribonuclease A.

Figure 5:
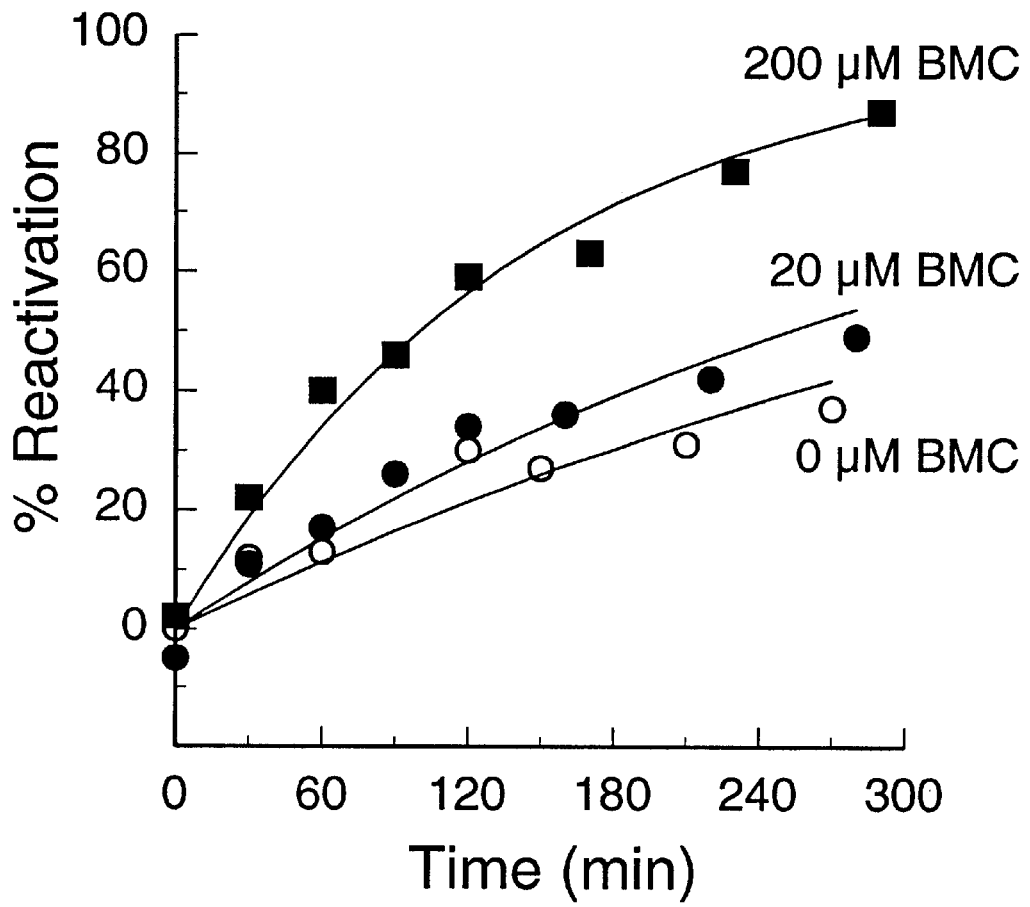
FIG. 5 is a graphical illustration of data from a one of the examples below.

The data from this assay are plotted in FIG. 5. Two lessons are apparent from these data. First, BMC significant catalysis of the regain of biological activity of a protein with scrambled disulfide bonds. Second, the total yield of active protein is significantly greater in the presence of BMC than in its absence. These properties make BMC a useful synthetic protein catalyst.

---

I claim:

1. A method of catalyzing the formation of disulfide linkages in a protein having non-native disulfide bonds to cause the protein to assume a biologically active conformation without the necessity for denaturation of the protein comprising the step of:

(a) exposing the protein having the non-native disulfide bonds to a dithiol protein folding catalyst, the protein folding catalyst being a non-protein dithiol molecule capable of forming an intramolecular disulfide bond and having a $pK_a$ of less than about 8.0 and an $E^{o\prime}$ of more than about –0.25 V.

2. The method of claim 1 wherein step (a) is performed in vitro.

3. A method of catalyzing the formation of disulfide linkages in a protein to cause the protein to assume a biologically active conformation comprising the step of:

(a) exposing the protein to a dithiol protein folding catalyst, the protein folding catalyst being a non-protein dithiol molecule having a $pK_a$ of less than about 8.0 and an $E^{o\prime}$ of more than about –0.25 V, wherein step (a) is performed in vivo in a unicellular organism.

4. The method of claim 3 wherein the protein is expressed in a heterologous host and step (a) is performed by adding the dithiol protein catalyst to the medium in which the host is cultured.

5. The method of claim 1 wherein the dithiol protein folding catalyst is N,N'-bis(1-mercaptoacetyl)-1,2-diaminocyclohexane (BMC).

6. A method for facilitating the proper expression of a protein expressed in a heterologous host in which the protein may be expressed with non-native disulfide bonds comprising the steps of:

(a) culturing the host under conditions favoring the expression of the protein in the host; and (b) exposing the protein in vivo during the culturing step to an effective amount of a dithiol synthetic protein folding catalyst so as to cause a greater amount of the protein to assume a biologically active conformation than would be the case if the protein folding catalyst was not added, the protein folding catalyst being a non-protein dithiol molecule having the capability of forming intramolecular disulfide bonds and having a $pK_a$ of less than about 8.0 and an $E^{o\prime}$ of more than about –0.25 V.

7. The method of claim 6 wherein the dithiol protein folding catalyst is BMC.

8. A method for facilitating the proper expression of a protein expressed in a heterologous host comprising the steps of:

(a) culturing the host under conditions favoring the expression of the protein in the host wherein at least some of the protein expressed includes a non-native disulfide bond; and (b) exposing the protein after the culturing step to an effective amount of a dithiol synthetic protein catalyst active to cause a greater amount of the protein to assume a biologically active conformation than would be the case if the protein folding catalyst was not added without the necessity for denaturation of the protein, the protein folding catalyst having the capability to form intramolecular disulfide bonds and being a non-protein dithiol molecule having a $pK_a$ of less than about 8.0 and an $E^{o\prime}$ of more than about –0.25 V.

9. The method of claim 8 wherein the dithiol protein folding catalyst is BMC.

* * * * *